(12) United States Patent
Kloster

(10) Patent No.: US 9,204,948 B2
(45) Date of Patent: Dec. 8, 2015

(54) BRUSHHEAD FOR A POWER TOOTHBRUSH WITH A WEDGE AND SPRING HANDLE INTERFACE

(75) Inventor: Tyler G. Kloster, Snoqualmie, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 289 days.

(21) Appl. No.: 13/993,103

(22) PCT Filed: Dec. 13, 2011

(86) PCT No.: PCT/IB2011/055624
§ 371 (c)(1),
(2), (4) Date: Jun. 11, 2013

(87) PCT Pub. No.: WO2012/085752
PCT Pub. Date: Jun. 28, 2012

(65) Prior Publication Data
US 2013/0255014 A1    Oct. 3, 2013

Related U.S. Application Data

(60) Provisional application No. 61/424,746, filed on Dec. 20, 2010.

(51) Int. Cl.
*A61C 17/22* (2006.01)
*A46B 13/02* (2006.01)
(Continued)

(52) U.S. Cl.
CPC ............ *A61C 17/222* (2013.01); *A46B 5/0095* (2013.01); *A46B 7/042* (2013.01); *A46B 13/023* (2013.01)

(58) Field of Classification Search
CPC .. A61C 17/222; A46B 5/0095; A46B 13/023; A46B 7/04; A46B 7/042; A46B 7/044
USPC ............ 15/22.1, 22.2, 176.1, 176.6, 145, 202
See application file for complete search history.

(56) References Cited

U.S. PATENT DOCUMENTS

| 3,535,726 A | 10/1970 | Sawyer |
| 3,680,169 A | 8/1972 | Thompson |
| 4,811,445 A | 3/1989 | Lagieski et al. |

(Continued)

FOREIGN PATENT DOCUMENTS

| CN | 201005230 Y | 3/2007 |
| DE | 8111798 U1 | 7/1981 |

(Continued)

OTHER PUBLICATIONS

DE3143196A1 (machine translation), 1983.*

*Primary Examiner* — Mark Spisich
*Assistant Examiner* — Andrew A Horton

(57) ABSTRACT

The brushhead (24) is part of a power toothbrush (10) which includes a handle portion (12) with a drive shaft (14) having a wedge-shaped free end (40) and a circumferential recess (36) in the external surface (35) adapted to receive a portion of a helical spring member (32). The brushhead includes a hollow neck portion (28) to receive the drive shaft. The hollow part of the neck portion includes a circumferential recess (38) in its interior surface (37) which is in registry with the recess on the drive shaft when the brushhead is operatively positioned on the handle, wherein the hollow portion includes a wedge-shaped recess (44) at the distal end thereof which receives in a mating relationship the wedge-shaped end of the drive shaft.

11 Claims, 2 Drawing Sheets

(51) Int. Cl.
*A46B 7/04* (2006.01)
*A46B 5/00* (2006.01)

(56) References Cited

U.S. PATENT DOCUMENTS

| | | | |
|---|---|---|---|
| 5,054,149 A * | 10/1991 | Si-Hoe et al. | 15/28 |
| 5,247,716 A | 9/1993 | Bock | |
| 5,987,681 A * | 11/1999 | Hahn et al. | 15/22.1 |
| 6,381,795 B1 | 5/2002 | Hofmann et al. | |
| 2004/0010872 A1 | 1/2004 | Chiang | |

FOREIGN PATENT DOCUMENTS

| | | | |
|---|---|---|---|
| DE | 3143196 A1 * | 5/1983 | A61C 17/02 |
| JP | 53029847 | 3/1978 | |
| JP | 10052447 A | 2/1998 | |
| JP | 2003339443 | 12/2003 | |
| JP | 2004057534 A | 2/2004 | |
| WO | 2007144821 A2 | 12/2007 | |

* cited by examiner

BRUSHHEAD FOR A POWER TOOTHBRUSH WITH A WEDGE AND SPRING HANDLE INTERFACE

REFERENCE TO RELATED APPLICATIONS

This application is a 371 of PCT/IB2011/055624, filed on Dec. 13, 2011, and claims the benefit of Provisional Application No. 61/424,746, filed on Dec. 20, 2010.

This invention relates generally to a brushhead for a power toothbrush, and more specifically concerns a mechanical interface between the brushhead and a handle portion of the toothbrush.

The interface arrangement between a movable, i.e. oscillating, brushhead and a handle of a power toothbrush is essential for proper operation of the toothbrush. The interface must provide the required axial retention force to hold the brushhead on during use but permit the brushhead to be conveniently pulled off by the user so that it can be replaced when the end of its lifetime has been reached or when the handle is to be cleaned or when another brushhead is to be used, such as for a family member. In addition, the interface must provide effective torque transfer between the drive shaft of the toothbrush, extending from the handle, and the brushhead. Any lost motion between the movement of the drive shaft and the corresponding movement of the brushhead results in inefficient operation, poor brushing efficacy and noise.

A mechanical interface, furthermore, should also be designed to accommodate reasonable manufacturing tolerances and material variations so that the axial retention force and the torque transfer characteristics are consistent from brushhead to brushhead. For instance, differences in material may result in a particular brushhead coming off during operation, which is undesirable. Also, the interface must be able to react all of the inertial forces produced during oscillation of the brushhead, in order to be both efficient and effective. For instance, if a portion of the mechanical interface is a spring, the spring stiffness must be at a particular level; if the spring stiffness is low, the efficiency of the torque transfer will be significantly reduced, resulting in reduced brush movement amplitudes and poor clinical efficacy.

Accordingly, it would be desirable for an interface assembly to provide a reliable and consistent axial retention force as well as efficient torque transfer, without the requirement of severe manufacturing tolerances.

Accordingly, disclosed herein is a power toothbrush and a brushhead therefor, wherein the brushhead assembly can be removed from and inserted onto a handle portion of the toothbrush, the handle portion including a drive shaft extending therefrom having a wedge-shaped free end and a peripheral recess in an external surface thereof to receive a portion of a spring member, the brushhead comprising: a brush member for cleaning teeth, mounted on a distal end of an extending neck portion, the neck portion being hollow over a portion of its length from a proximal end thereof to receive the drive shaft from the handle portion, wherein the neck portion includes a peripheral recess in an internal surface of the hollow portion thereof, which is in registry with the recess in the drive shaft when the brushhead assembly is operatively positioned on the handle, into which recesses a circular spring member is received, to provide reliable axial retention of the brushhead assembly on the drive shaft, and wherein the hollow portion of the neck at an upper end of the hollow portion includes a mating wedge-shaped recess to cooperatively receive the wedge-shaped end of the drive shaft in a sufficiently tight relationship to provide efficient torque transfer between the drive shaft and the brushhead assembly.

Figures 1, 2:
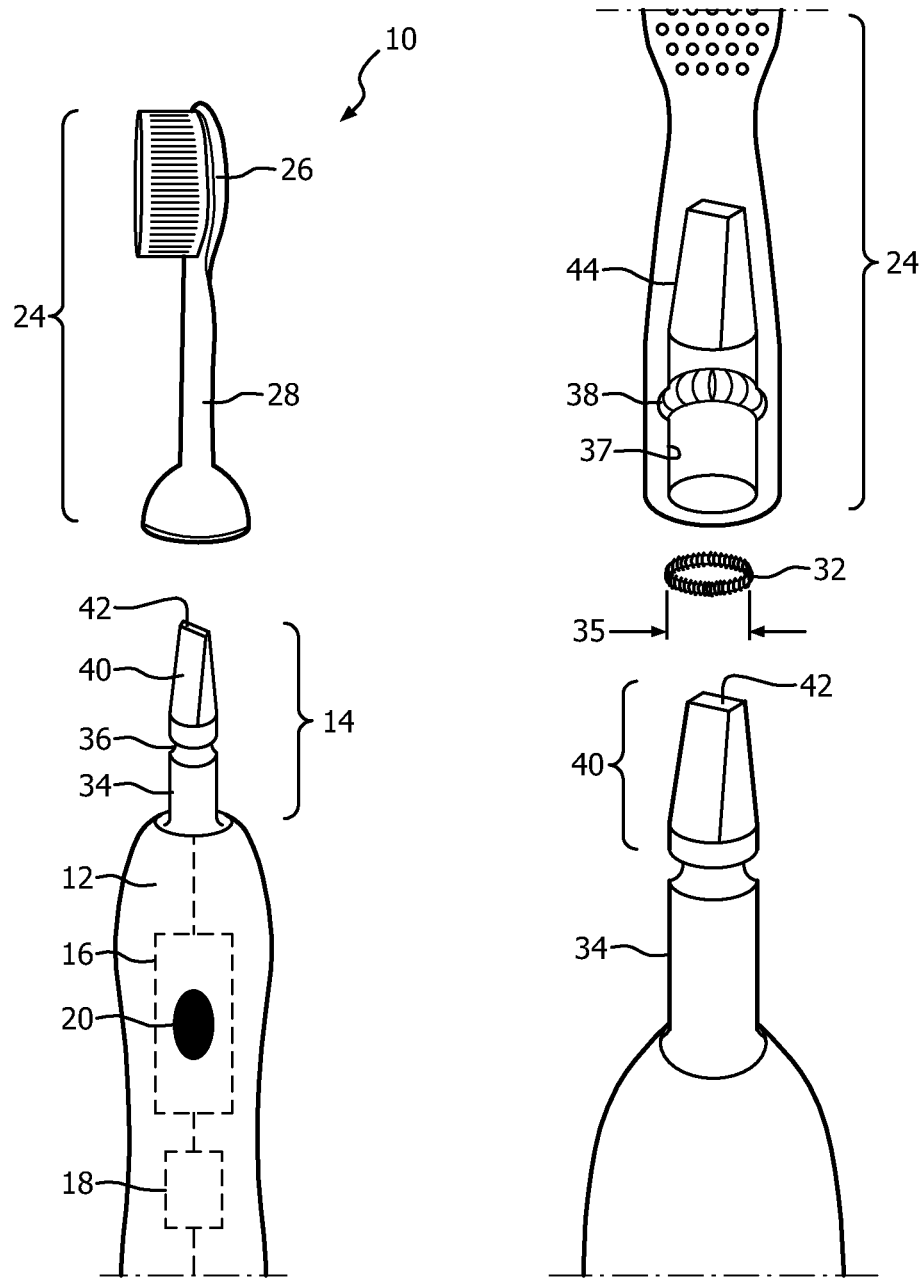
FIG. 1 is a simplified elevational exploded view of a power toothbrush incorporating the brushhead/handle interface disclosed herein.
FIG. 2 is an exploded view showing in more detail the brushhead/handle interface arrangement of FIG. 1, wherein the interface is shown partially in cross section

FIG. 1 shows a power toothbrush generally at 10. It includes a handle portion 12, with a drive shaft 14 extending from the top of the handle. The drive shaft 14 is part of a drive assembly 16 in the handle, powered by a battery 18 which is typically rechargeable. An on/off switch 20 controls the operation of the toothbrush. The drive assembly 16 can take various forms. In one embodiment, the drive assembly is an electromagnetic motor which oscillates the drive shaft through a selected angle, for instance within the range of 5-20°, preferably approximately 11°, at a frequency within the range of 200-300 Hz, preferably approximately 260 Hz. These specifications typically provide effective cleaning. However, it should be understood that other drive arrangements can be used.

The toothbrush 10 also includes a brushhead assembly portion 24. The brushhead assembly portion 24 includes a conventional brush member 26 for contact with, and cleaning of, the teeth, and an extended neck portion 28. The bristle member 26 is mounted on the distal end of neck portion 28. Neck portion 28 mates with handle portion 12 through a brushhead/handle interface which includes specific mechanical characteristics within the neck portion of the brushhead which provide a reliable connection between the brushhead 24 and drive shaft 14.

Figure 3:
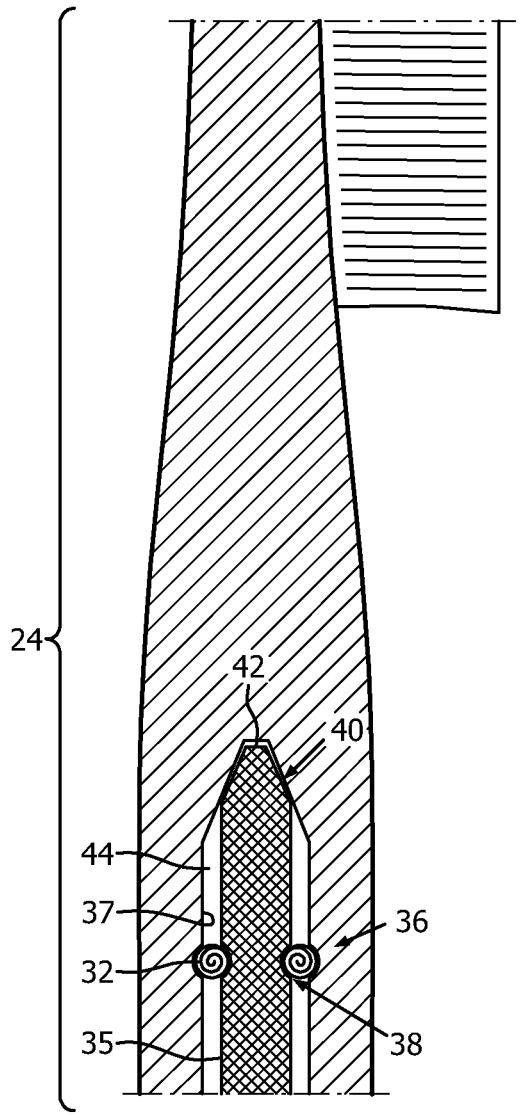
FIGS. 3 and 4 show orthogonal cross-sectional diagrams of the brushhead/handle interface of FIG. 1.
Figure 4:
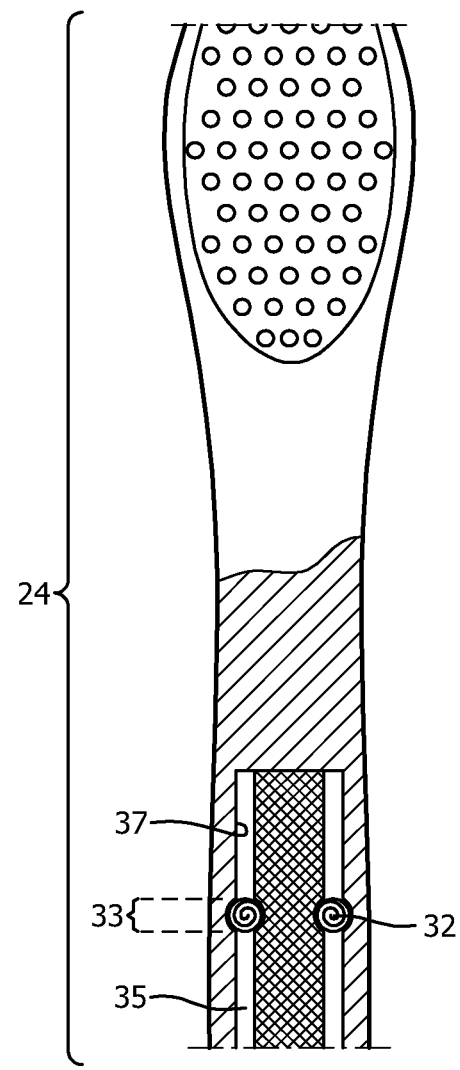

Referring now to FIGS. 2, 3 and 4, brushhead assembly portion 24 is retained on and removable from drive shaft 14 by a spring arrangement/member 32. The spring member in the embodiment shown is a coil spring which is a spring having a helical winding formed in a circle. For instance, the two ends of a helical spring can be welded together to form a circle of desired dimension. One such spring is available from Bal Seal Engineering, Inc. Spring member 32 is made from spring steel. In the toothbrush embodiment shown, the diameter 33 of the coil itself is a few millimeters, i.e. ½ to 3 mm. The diameter 33 of the spring 32 (FIG. 4), fitting between the external surface 35 of drive shaft 14 and the internal surface 37 of the neck 28 of the brushhead assembly 24, is between 5-10 mm.

The external surface 35 of the drive shaft and the internal surface 37 of the neck of the brushhead assembly, which is hollow in a lower region thereof, include recesses 36, 38, respectively, which are in registry when the brushhead is operatively positioned on the handle, as shown most clearly in that arrangement in FIGS. 3 and 4.

The size and diameter of the helical coil spring in the embodiment shown is adapted for a toothbrush embodiment. Different spring sizes, i.e. different coil diameters and different spring diameters are possible depending upon the particular application, such as for personal care appliances other than toothbrushes. The depth of the respective recesses 36 and 38 is approximately one-quarter to one-half of the coil diameter. Typically, the recess in the neck will be deeper than the recess on the drive shaft, as it is typically more desirable to have the spring retained within the neck when the brushhead is removed from or inserted onto the drive shaft. However, it could be the opposite as well, i.e. the recess on the drive shaft could be deeper so that the spring is retained on the drive shaft during removal and insertion of the brushhead. This above spring/recess arrangement provides a reliable axial retention force; in the embodiment shown, it is typically in the range of 5-15 newtons. This retention force maintains the brushhead assembly 24 on the drive shaft 34 during operation of the toothbrush (i.e. so that it will not "walk off" during operation), yet allows the brushhead to be conveniently removed by a typical user, for replacement by a new or different brushhead or for cleaning of the handle.

Referring still to FIGS. 2-4, drive shaft 14 includes a wedge-shaped portion 40 at the upper end thereof. In the embodiment shown, the length of the wedge portion is approximately 5-15 mm, preferably 10 mm. The distal end 40 of the wedge portion is 2-4 mm long and approximately 1-2 mm wide. Typically, the edges of the end 40 will be radiused. The angle of the wedge portion is in the range of 5-30°, preferably approximately 20°.

The hollow part of the neck portion includes a mating wedge-shaped recess 44 at the upper end thereof to receive the wedge-shaped portion 40 of the drive shaft. Typically, the configuration of the wedge-shaped recess 44 will closely match the wedge-shaped portion 40 of the drive shaft, although the angles of the two recesses can be slightly different, i.e. a few degrees difference. The resulting wedge-shaped combination (drive shaft portion and neck recess) provides a reliable, high efficiency torque transfer between drive shaft 14 and brushhead 24. The combination of the coil spring nested in the two recesses 36 and 38 and the wedge combination also results in the interface being effective, i.e. robust, relative to a reasonable range of dimensional tolerances of the various components of the interface, i.e. the interface can accommodate some differences in dimensions between the drive shaft and the neck, and some differences in material composition. The arrangement of the wedge-shaped drive shaft and the mating wedge-shaped recess in the neck insures that the mating surfaces will be pulled together into direct contact without any gaps between the two elements. The coil spring, as it is positioned in the two recesses, will take up tolerances in the respective exterior diameter of the drive shaft and/or the interior diameter of the hollow part of the neck, eliminating any motion/play between the two elements.

The above arrangement thus provides a structurally simple but robust interface between a drive shaft and a brushhead assembly, with a reliable, low variation axial retention force, as well as efficient torque transfer.

Although a preferred embodiment has been disclosed for purposes of illustration, it should be understood that various changes and modifications and substitutions could be made in the preferred embodiment without departing from the spirit of the invention as defined by the claims which follow:

The invention claimed is:

1. A brushhead assembly for a power toothbrush, wherein the brushhead assembly can be removed from and inserted onto a handle portion of the toothbrush, the handle portion including a drive shaft extending therefrom having a wedge-shaped free end and a peripheral circumferential recess in an external surface thereof to receive a portion of a helical coil spring member having the form of a circle, the brushhead comprising:
   a brush member for cleaning teeth, mounted on a distal end of an extending neck portion, the neck portion being hollow over a portion of its length from a proximal end thereof to receive the drive shaft from the handle portion, wherein the neck portion includes a peripheral circumferential recess in an internal surface of the hollow portion thereof, which is in registry with the recess in the drive shaft when the brushhead assembly is operatively positioned on the handle, into which recesses the helical coil spring member having the form of a circle is received, to provide reliable axial retention of the brushhead assembly on the drive shaft, and wherein the hollow portion of the neck at an upper end of the hollow portion includes a mating wedge-shaped recess to cooperatively receive the wedge-shaped end of the drive shaft in a sufficiently tight relationship to provide efficient torque transfer between the drive shaft and the brushhead assembly.

2. The brushhead assembly of claim 1, wherein the relationship between the end of the drive shaft and the recess in the neck portion is tight enough to remove substantially all play between the drive shaft and the brushhead assembly.

3. The brushhead assembly of claim 1, wherein the recess in the neck portion of the brushhead assembly is deeper than the recess in the drive shaft, so that the spring is retained within the neck when the brushhead assembly is removed from the drive shaft.

4. The brushhead assembly of claim 1, wherein the angle of the wedge-shaped recess is in the range of 5° to 30°.

5. The brushhead assembly of claim 4, wherein the upper end of the wedge-shaped recess has a width in the range of 1-2 mm, a length in the range of 2-4 mm, and wherein the length of the wedge-shaped recess is within the range of 5-15 mm.

6. The brushhead assembly of claim 1, wherein the angle of the wedge-shaped recess is substantially the same as the angle of the wedge-shaped free end of the drive shaft.

7. A power toothbrush, comprising:
   a handle portion having a drive assembly with an extending drive shaft with a wedge-shaped free end, the drive shaft including a circumferential recess in an external surface thereof;
   a brushhead having a brush member for cleaning of teeth and an extending neck portion upon which the brush member is mounted at a distal end thereof, the neck portion being hollow over a portion of its length from a proximal end thereof, adapted and configured to receive the drive shaft from the handle portion, including a peripheral circumferential recess in an internal surface of the hollow portion thereof, which is in registry with the recess in the drive shaft when the brushhead assembly is operatively positioned on the handle, and wherein the hollow part of the neck portion includes a mating wedge-shaped recess at a distal end thereof to cooperatively receive the wedge-shaped free end of the drive shaft in a sufficiently tight relationship to provide efficient torque transfer between the drive shaft and the brushhead; and
   a helical coil spring member in the form of a circle, adapted and configured to fit within the circumferential recess and the peripheral recess which are in registry when the brushhead is operatively positioned on the handle, providing reliable axial retention of the brushhead on the drive shaft.

8. The power toothbrush of claim 7, wherein the recess in the neck portion is deeper than the recess in the drive shaft so that the spring member is retained in the neck when the brushhead is removed from the handle.

9. The power toothbrush of claim 7, wherein the wedge-shaped free end of the drive shaft has a forward edge which is at a right angle to an axis of the drive shaft and wherein the wedge-shaped free end of the drive shaft has opposing surfaces which angle inwardly toward each other, is substantially the same as the angle of the wedge-shaped recess in the neck.

10. The power toothbrush of claim 9, wherein the angle is within the range of 5° to 30°.

11. The power toothbrush of claim 7, wherein the widths of the wedge-shaped free end of the drive shaft and the wedge-shaped recess in the neck are both substantially the same, 1-2 mm, the lengths are both substantially the same, 2-4 mm and the lengths of the wedge-shaped end and wedge-shaped recess are both substantially the same, 5-15 mm.

* * * * *